United States Patent [19]

Yu et al.

[11] Patent Number: 5,177,082
[45] Date of Patent: Jan. 5, 1993

[54] HUPERZINES AND ANALOGS

[76] Inventors: Chao-mei Yu, Zhejiang Academy of Medicine, Tian Muo Shan Str. Hangzhou; Xi-can Tang; Jia-sen Liu, both of 319 Yue-Yang Road, Shanghai 200031; Yan-yi Han, Tian Muo Shan Str., Hangzhou, all of China

[21] Appl. No.: 599,541

[22] Filed: Oct. 18, 1990

Related U.S. Application Data

[63] Continuation of Ser. No. 305,882, Feb. 2, 1989, abandoned, which is a continuation of Ser. No. 936,005, Nov. 28, 1986, abandoned, which is a continuation-in-part of Ser. No. 795,064, Nov. 5, 1985, abandoned.

[51] Int. Cl.⁵ .................. A61K 31/435; C07D 211/22
[52] U.S. Cl. ................................ 514/286; 514/295; 546/63; 546/97
[58] Field of Search .................. 546/63, 97; 514/286, 514/295

[56] References Cited

U.S. PATENT DOCUMENTS 4,929,731  5/1990  Kozikowski et al. .............. 546/97

OTHER PUBLICATIONS

Thompson, et al., New England J. of Medicine vol. 323(7), 1990, pp. 445–448.
New Drugs and Clin. Res. (China) Published Jul. 25, 1985, vol. 4, No. 4:235.
Acta Pharmacologica Sinica, 1986 Mar: 7(2) 110–113.
Can. J. Chem. vol. 64, 837–839 (1986).
Journal of the Taiwan Pharmaceutical Association vol. 36 No. 1,1–7 (1984).
Merck Index, Ninth Edition Item #8179 Selagine.
Canadian Journal of Chemistry, 1989 67 (10) 1538–1540.

Primary Examiner—Robert T. Bond
Assistant Examiner—E. C. Ward
Attorney, Agent, or Firm—George M. Gould; William G. Isgro

[57] ABSTRACT

The invention relates to compounds of the formulas

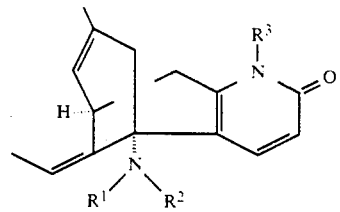

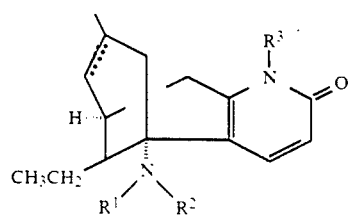

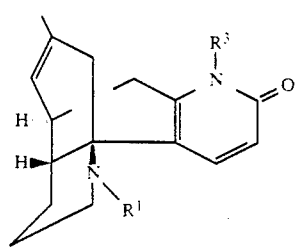

wherein $R^1$, $R^2$ and $R^3$ independently are hydrogen or lower alkyl, and the dotted (. . .) line is an optional double bond, and their pharmaceutically acceptable acid addition salts. The compounds of formulas I, II and III possess marked anticholinesterase activity and are useful as analeptic agents and as agents for the treatment of senile dementia and myasthenia gravis.

10 Claims, No Drawings

HUPERZINES AND ANALOGS

CROSS REFERENCE TO RELATED APPLICATIONS

This is a continuation of application Ser. No. 07/305.882 filed Feb. 2, 1989, now abandoned which is a Rule 60 continuation of Ser. No. 936.005 filed Nov. 28, 1986, now abandoned which is a continuation-in-part application of Ser. No. 06/795,064 filed Nov. 5, 1985, now abandoned.

BRIEF SUMMARY OF THE INVENTION

The invention relates to compounds of the formulas

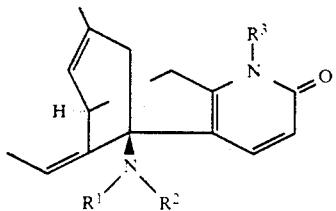

I

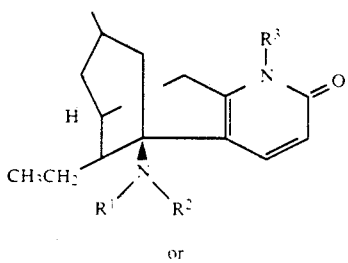

II or

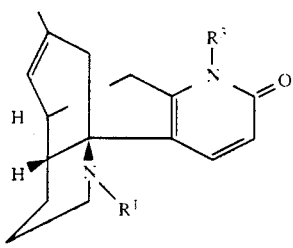

III wherein $R^1$, $R^2$ and $R^3$ independently are hydrogen or lower alkyl, and the dotted ( . . . ) line is an optional double bond, and their pharmaceutically acceptable acid addition salts. The compounds of formula I, II, and III possess marked anticholinesterase activity and are useful as analeptic agents and as agents for the treatment of senile dementia and myasthenia gravis.

DETAILED DESCRIPTION OF THE INVENTION

The invention relates to compounds of the formulas

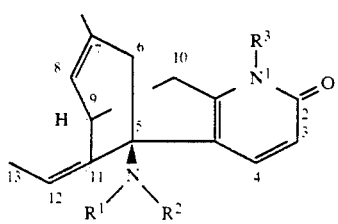

I

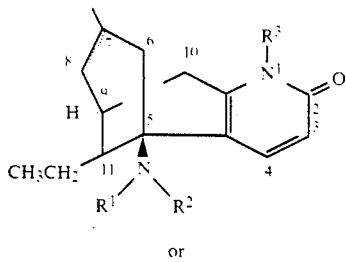

II or

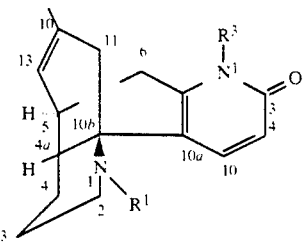

III wherein $R^1$, $R^2$ and $R^3$ independently are hydrogen or lower alkyl, and the dotted ( . . . ) line is an optional double bond, and their pharmaceutically acceptable acid addition salts.

As used herein, the term "lower alkyl" denotes a radical of 1 to 7 carbon atoms, for example, methyl, ethyl, propyl, isopropyl, isobutyl, tertiary butyl, pentyl, heptyl and the like.

The compounds of formulas I, II and III can be prepared as hereinafter described. More particularly, the compounds of formulas I and III, wherein $R^1$, $R^2$ and $R^3$ are hydrogen, which are alkaloids, can be prepared from the naturally occuring plant Huperzia serrata by extraction and subsequent chromatographic separation. Conveniently, the extraction and separation of the desired (5R, 9R, 11E)-5-amino-11-ethylidene-5,6,9,10-tetrahydro-7-methyl-5,9-methanocycloocta[b]pyridin-2(1H)-one (Huperzine A) can be effected by known procedures. For instance, a solvent such as an alkanol, for example, ethanol, can be utilized. The extracts obtained can be evaporated and the residue further separated by sequential treatment and extraction as follows. The residue is treated with an inorganic acid, for example, hydrochloric acid. The aqueous phase is neutralized with a base, for example, ammonia or sodium hydroxide, and the total alkaloids extracted by a solvent, for example, chloroform. This sequence can be repeated many times. The final extract can be chromatographed on a silica gel column. Fractions for the chromatography are analyzed by TLC and those with single spots are combined to yield substantially pure Huperzine A. To obtain pure Huperzine A, it can be rechromatographed and recrystallized by known methods, as for example, from a methanol/acetone mixture.

The crude material isolated from later fractions of the chromatography is a minor component which, when rechromatographed on silica gel using, for example, a solvent system of chloroform, acetone and methanol, and recrystallized, for example, from acetone, yields pure (4aR, 5R, 10bR)-1,2,3,4,4a,5,6,10b-octahydro-12-methyl-5,10b-propeno-1,7-phenanthrolin-8(7H)-one (Huperzine B).

The other compounds of formulas I and III can be prepared by alkylation of a compound of formula I or III, wherein $R^1$, $R^2$ and $R^3$ are hydrogen, respectively.

More specifically, the alkylation of a compound of formula I, wherein $R^1$, $R^2$ and $R^3$ are hydrogen, that is, Huperzine A, can be effected utilizing known procedures. For example, if the mono-alkylamino ($R^1$ is alkyl) derivative is desired, Huperzine A is reacted with an alkyl halide, such as, methyl iodide under standard conditions. If the dialkylamine ($R^1$ and $R^2$ are alkyl) derivative is desired, the monoalkylamino derivative is treated further with an alkyl halide, such as, methyl iodide. If the dimethylamine ($R^1$ and $R^2$ are alkyl) derivative is desired, it can also be prepared by reacting Huperzine A with a mixture of formic acid and formaldehyde under standard conditions. If the trialkyl ($R^1$, $R^2$ and $R^3$ are alkyl) derivative of Huperzine A is desired, Huperzine A is treated with a dialkylsulfate, such as dimethylsulfate, utilizing standard conditions with heating. In each instance, the desired derivatives can be separated by chromatography and crystallization, or the like.

A compound of formula II can be prepared from the corresponding compound of formula I by selective reduction to either reduce the exocyclic double bond or both the exocyclic and endocyclic double bonds. The exocyclic double bond can be reduced by catalytic hydrogenation utilizing platinum in an alkanol, such as, ethanol, under known conditions. The exocyclic and endocyclic double bonds can be reduced by catalytic hydrogenation utilizing platinum in an organic acid, such as, acetic acid, under known conditions. In each instance, the desired derivatives can be seaprated by chromatography and crystallization, or the like.

The compounds of formula III, wherein $R^1$ and $R^2$ are hydrogen, that is, Huperzine B, can be recovered during the separation and recovery of Huperzine A. More specifically, (4aR, 5R, 10bR)-1,2,3,4,4a,5,6,10b-octahydro-12-methyl-5,10b-propeno-1,7-phenanthrolin-8(7H)-one (Huperzine B) can be recovered, as previously described, in the isolation of Huperzine A, initially, as a crude material purified from the later fractions of the chromatography.

The alkylation of a compound of formula III, wherein $R^1$ and $R^3$ are hydrogen, that is, Huperzine B, can be effected utilizing known procedures. For example, if the mono-alkylamino($R^1$ is alkyl) derivative is desired, Huperzine B is reacted with an alkyl halide, such as, methyl iodide, under standard conditions. If the monomethyl derivative ($R^1$ = methyl) is desired, it can also be prepared by reacting Huperzine B with a mixture of formic acid and formaldehyde under standard conditions. If the dialkyl ($R^1$ and $R^3$ are alkyl) derivative of Huperzine B is desired, Huperzine B is treated with a dialkylsulfate, such as, dimethylsulfate, utilizing standard conditions with heating. In each instance, the desired derivative can be separated by chromatography and crystallization, or the like.

The compounds of formulas I, II and III form acid addition salts with inorganic or organic acids. Thus, they form pharmaceutically acceptable acid addition salts with both pharmaceutically acceptable organic and inorganic acids, for example, with hydrohalic acid, such as, hydrochloric acid, hydrobromic acid, hydroiodic acid, other mineral acid salts, such as, sulfuric acid, nitric acid, phosphoric acid, perchloric acid or the like, alkyl, and mono-aryl sulfonic acids, such as, ethanesulfonic acid, toluenesulfonic acid, benzenesulfonic acid, or the like, other organic acids such as acetic acid, tartaric acid, maleic acid, citric acid, benzoic acid, salicylic acid, ascorbic acid and the like. Non-pharmaceutically acceptable acid addition salts of the compounds of formulas I, II and III can be converted into pharmaceutically acceptable acid addition salts via conventional metathetic reactions whereby the non-pharmaceutically acceptable anion is replaced by a pharmaceutically acceptable anion; or alternatively, by neutralizing the non-pharmaceutically acceptable acid addition salt and then reacting the so-obtained free base with a reagent yielding a pharmaceutically acceptable acid addition salt.

The compounds of formulas I, II and III and their pharmaceutically acceptable acid addition salts exhibit strong cholinesterase inhibiting effects, relatively low toxicity, a large therapeutic index and are superior to physostigmine. Accordingly, the compounds are useful in the treatment of myasthenia gravis and senile dementia. The activity of the compounds of formula I, II and III can be demonstrated in warm-blooded animals, in accordance with known procedures, as hereinafter described.

More specifically, Huperzine A, a representative compound of the invention, is a potent reversible cholinesterase inhibitor which is very selective for specific acetylcholine esterase and it is markedly different from physostigmine. It increased the amplitude of muscle contraction produced by the indirect electrical stimulation of nerves in vitro and using neuromuscular preparations. It also has marked blocking effects against curare. A 1/138 of the $LD_{50}$ dosage of Huperzine A can strengthen the memory functions of normal male rats (Y-maze and brightness discrimination test). The i.p. acute toxicity of Huperzine A is about one-half that of physostigmine in rats and mice. Six months of sub-acute toxicity tests on rats, rabbits and dogs showed that when ninety times the dosage of Huperzine A needed for clinical patients to treat myasthenia gravis and 750 times the equired dosage to treat senile dementia was used, no noticeable pathological changes of internal organs were observed. Mutagenicity test (Ames test) and rat and rabbit teratogenicity tests were all negative for Huperzine A. 3H-labelled Huperzine A was used to carry out pharmacodynamic, distribution and in vivo metabolism research. These studies showed that when 3H-Huperzine A was used the concentration curve matched the open, two compartment model. Its $t_{\frac{1}{2}\alpha} = 5.4$ minutes and $t_{\frac{1}{2}\beta} = 119.5$ minutes. There was a certain distribution in the brain which shows that it can pass the blood-brain barrier. There was only a minute quantity of radioactivity in every organ examined after twenty-four hours. Seven days after a single dose 86.1% was eliminated in the urine (84.9% of the excreted drug appearing within twenty-four hours), and 5.5% was eliminated through feces.

Enhancing the Contraction Amplitude of Striated Muscles

1. In Vitro Phrenic Nerve/Diaphragm Preparations of Rats.

After the fast decapitation of a rat, the thoracic cavity was opened and the right diaphragm with attached phrenic nerve was removed. After placing it in a Tyrode's solution (37° C. constant temperature), gassed with 95% oxygen+5% $CO_2$, electrical stimulation (1–10 V, 0.5 ms, 1 c/10 s) of the phrenic nerve was used to produce muscle contraction. A transducer was used to record the contraction amplitude on a panel recorder. The results are listed in Table 1. When Huperzine A was used in a 0.348 μM concentration, it increased the electrically induced contraction amplitude of muscle by 19%. This action corresponded with the concentration of Huperzine A, showing a very good dose-response relationship. The action of the Huperzine A was slightly weaker than that of physostigmine and neostigmine but much stronger than that of galanthamine.

TABLE 1

The enhancing Effects of Huperzine A on In Vitro Rat Nerve/Diaphragm Muscle Contraction

| Drug | Enhancement of Muscle Contraction Amplitude, 50% Concentration (μM) | Strength of Effect |
|---|---|---|
| Huperzine A | 0.440 | 1.00 |
| Physostigmine | 0.245 | 1.79 |
| Neostigmine | 0.272 | 1.61 |
| Galanthamine | 4.2 | 0.10 |
| Huperzine B | 4.8 | 0.09 |

2. Anesthesized Rat and Rabbit Sciatic Nerve/Tibialis Muscle Preparation

Anesthesia was produced in rats by ip injections of 30 mg/kg of pentobarbital and in rabbits by iv injections of 1 g/kg of urethane. Electric stimulation of the periphery of the sciatic nerve (5–10 V, 0.5 ms, 1 c/10 s) caused tibialis contraction which was recorded on smoked paper. The rats or rabbits given iv injections of 30 μg/kg of Huperzine A showed enhancement of the amplitude of the electrically stimulated muscle contraction. Injections of physostigmine, i.v., also enhanced the rabbit's tibialis muscle contraction amplitude but to a lesser degree than that observed for the rats. The potency of Huperzine A in these tests was 1.7 and 4 times that of physostigmine (Table 2). Tubocurarine (0.3 mg/kg iv) completely blocked the electrically induced muscle contraction. After twenty minutes of sustained stimulation, the tibialis muscle contraction amplitude gradually reached the amplitude observed before the injection of tubocurarine. If Huperzine A (40–60 μg/kg i.v.) was given after the i.v. tubocurarine there was marked inhibition of the tubocurarine blockade. Five minutes later, the amplitude of the tibialis muscle contraction was comparable to that seen in the absence of tubocurarine.

TABLE 2

The strengthening Effects of Huperzine A on Whole Neuromuscular Preparations.

| Drug | Lowest Effective Dosage for Enhancing Muscle Contraction (μg/kg i.v.) | | | | | |
|---|---|---|---|---|---|---|
| | Rats | Strength of Effect | | Rabbits | Strength of Effect | |
| Physostigmine | 50 | 1.0 | | 120 | 1.0 | |
| Galanthamine | 500 | | 1.0 | 500 | | 1.0 |
| Huperzine A | 30 | 1.7 | 16.6 | 30 | 4.0 | 16.6 |

ENHANCING THE LEARNING AND MEMORY FUNCTIONS OF RATS

To demonstrate an effect on the learning process a "Y" maze conditioned reflex test was used. Each animal was required to go through 10 successive shock-free runs to be classified as learned. The control animals accepted 11.9±4.9 shocks before achieving the learned state while those receiving 1/50 of the $LD_{50}$ of Huperzine-A (0.1 mg/kg, iv) took 6.8±2.8 and those receiving physostigmine (0.08 mg/kg, iv) took 7.9±3.5.

To evaluate the impact on the memory function, preconditioned animals going through 5 shock-free runs were used as learned animals. After 48 hours the drug-free (control) animals required 14.4±8.9 shocks to become learned. With Huperzine A (0.03 mg/kg, ip) only 6.8±7.2 shocks were required while with physostigmine (0.15 mg/kg) 6.4±3.7 shocks were needed to achieve the learned state.

THE IN VIVO DISPOSITION OF $^3$H-HUPERZINE A

Rats were lightly anesthetized with sodium pentobarbital supplemented with ether and a cannula was placed in the carotid artery. After the animals awoke 1,5,15 and 30 minutes and 1,2 and 3 hours after administering iv injections of 375 μCi/kg of $^3$H-Huperzine A, 0.2 ml of blood was taken from the carotid artery and 0.8 ml of water plus one drop of aqueous ammonia (pH 10) were added to each sample. After adding 5 ml of 1,2 dichloroethane, extraction was effected with the aid of a vortex mixer for three minutes. The aqueous phase was extracted two more times with dichloroethane. After combining the organic phases, the liquid was evaporated to dryness and the residue was placed on silica impregnated filter paper and developed with a mixture of chloroform:acetone:methanol: aqueous ammonia (49:49:1:1) solvent. After chromatographic separation, the 0.5×2 cm band corresponding to the position of non-radioactive Huperzine A was cut out and examined by liquid scintillation techniques. The time curve of $^3$H-Huperzine A in the blood disclosed an open, two compartment model of distribution. The eliminated phase rate constant and half-life period were separately $\alpha = 0.129$ min$^{-1}$, $t_{\frac{1}{2}\alpha} = 5.4$ min, $\beta = 0.0058$ min$^{-1}$, $t_{\frac{1}{2}\beta} = 119.5$ min, $K_{21} = 0.0366$, $K_{10} = 0.0204$, $K_{12} = 0.0778$, Vc = 1.04 l/kg, Vd = 3.66 l/kg, the elimination rate was $K_{10}$ and Vc = 21.17 ml/min/kg.

After giving 250 μCi/kg by iv injections of $^3$H-Huperzine A to the rats, they were sacrificed at different times by bloodletting and the radioactivity contents of the organs were measured. Fifteen minutes after the drug was given, the kidney and liver had the highest contents, the lungs, spleen and heart had less and the fat and brain had the least. Two hours after the drug was given, the radioactivity in the other tissues was markedly lower while that in the brain rose slightly. Twelve hours after giving the drug, the radioactivity in each tissue was close to zero.

Intragastric (ig) injections of $^3$H Huperzine A (375 μCi/kg) were given 14 hours after the stomachs of the rats were empty and 10 μl of blood was removed from the tip of the tail for measurement of radioactivity. Twenty minutes after the ig injection, the radioactivity in the blood had risen noticeably. It reached a peak in 45–60 minutes after the ig injection and then slowly decreased. Seven hours after the drug was given, the radioactivity in the blood was still relatively high.

After giving a 250 μCi/kg iv injection of $^3$H-Huperzine A, the urine was collected from 0–6 and 6–24 hours, control urine was collected separately. After chromatographic analysis, a radioactive peak (I) was detected in the $R_f$ 0.65–0.71 area which was identical to that of unaltered $^3$H-Huperzine A. Another radioactive peak (II) was found in the $R_f$ 0.17–0.21 area and represented a metabolite of the parent compound. The ratio of the two peaks (II:I) gradually increased with the time of urine collection. The II:I ratio was 0.4 after six hours and it was 1.4 in the 6-24 hour period. Thus the drug metabolite was more slowly eliminated into the urine after going through the in vivo process.

Using equilibrium dialysis, it could be shown that the protein binding of $^3$H-Huperzine A in the plasma of normal mice was $17.2 \pm 4.1\%$.

INHIBITING THE ENZYME ACTIVITY OF CHOLINESTERASE

Red blood cell membranes of rats were used as the source for the true cholinesterase with a substrate concentration of 0.3 mM of S-acetylthiocholine iodide. The source for pseudocholinesterase was 0.1 ml of rat blood serum and the substrate was 0.4 mM S-butyrylthiocholine iodide. The Ellman colorimetric method was used to measure the enzyme activity. The percentage of enzyme activity remaining was plotted against negative logarithm (pI) of the drug concentration and the $pI_{50}$ (the negative logarithm of the gram molecule concentration of the drug required to inhibit the enzyme activity 50%) was derived. Huperzine A inhibited pseudocholinesterase less and true cholinesterase more than physostigmine and neostigmine (Table 3).

A certain quantity of true cholinesterase was mixed with a certain quantity of inhibitor and the enzyme activity was measured at different times after mixing. After the Huperzine A and enzyme were mixed 20 to 30% inhibition was seen very quickly, which did not change over a 6 minute period. The same response was noted for the reversible cholinesterase inhibitors:choline chloride and galanthamine. The irreversible cholinesterase inhibitor DFP, however, yielded increased inhibition with incubation time. Huperzine A yielded inhibition vs time responses similar to those of choline chloride and galanthamine, but different from DFP. Removing the enzyme preparation from a mixture with Huperzine A and then washing restored the activity of the enzyme to $94.4 \pm 4.9\%$ of the preincubation value.

The above results show that Huperzine A is a reversible cholinesterase inhibitor.

TABLE 3

Inhibitory Effects of Huperzine A on Cholinesterase

| Drug | Inhibition of Cholinesterase ($pI_{50}$) | |
|---|---|---|
| | Blood serum | Red Blood Cells |
| Huperzine A | 4.2 | 7.2 |
| N-dimethyl huperzine A | $1.2 \times 10^{-2}$ M ineffective | 3.8 |
| N-trimethyl-huperzine A | $1.1 \times 10^{-2}$ M ineffective | 3.5 |
| 11,12-dihydro-huperzine A | 4.9 | 6.2 |
| tetrahydro-huperzine A | 4.3 | 5.6 |
| N-acetyl huperzine A | $1.1 \times 10^{-2}$ M ineffective | <2.5 |
| huperzine B | 3.7 | 6.3 |
| N-methyl huperzine B | 3.5 | 4.1 |
| Physostigmine | 5.95 | 6.65 |
| Neostigmine | 5.45 | 6.65 |
| Galanthamine | 4.9 | 5.7 |

TOXICITY TESTS

1. Acute Toxicity

A single toxic dose of Huperzine A to mice, rats, rabbits and dogs yielded the typical symptoms of cholinesterase inhibitor poisoning, such as whole body muscle fiber twitching, drooling, tears, increase bronchial secretions and incontinence of feces and urine. The acute toxicity of physostigmine was 1.25 and 1.08 times greater than Huperzine A in mice and rats and both were greater than that of galanthamine. The iv route was most toxic and the ig route least toxic for Huperzine A in rats and mice (Table 4). Ten conscious rabbits were separately given im or iv injections of 0.5-2 mg/kg of Huperzine A and were observed to display the above mentioned toxic side effects for 3-4 hours. One of the two rabbits given iv injections of 2 mg/kg of Huperzine A died. This dosage was 66 times the effective dosage for enhancing muscle contraction. Six dogs anesthesized with chloralose were separately given 0.306 and 1 mg/kg iv injections of Huperzine A with no noticeable effects on the carotid artery blood pressure and EKG.

2. Subacute Toxicity

Rats: 20 male rats were separated into two groups. The first group was given 0.3 mg/kg ip injections of Huperzine A for 51 days while the second group (controls) received the same schedule of distilled water. The routine blood tests (the percent hemoglobin, numbers of red and white cells as well as platelets), zinc turbidity, creatinine and urea nitrogen were all normal. In another test 70 rats were divided into 6 groups. One was given ip injections of 0.5 mg/kg (10 rats) another 1.5 mg/kg (10 rats) of Huperzine A and a third group (10 rats) received only distilled water each day for 90 days. The remaining groups were given ig injections of 1.5 mg/kg (15 rats), 3 mg/kg (15 rats) of Huperzine A each day for 180 days.

A small number of those in groups given large dosages died within 30-150 days while those which survived were sacrificed for examination. The glutamic-pyruvic transaminase values of individual rats from the group given ip and ig injections of 1.5 mg/kg dosages were slightly higher than those of the control group. However, no noticeable effects on the routine blood tests, blood sugar, urea nitrogen, zinc turbidity, musk oxaphenol turbidity and ECG were detected. Microscopic examination of various organ sections showed that the heart muscle had dot-shaped and slice-shaped inflamed areas accompanied by myocardial cell denaturation atrophy. Cerebral spongiocyte growth and myophagia was noted and a small number of rats had sperm cell growth inhibition and interstitial growth. No abnormalities were observed in the other organs.

Rabbits and dogs: there were 20 rabbits divided into four groups. They were separately given im injections of 0.6 mg/kg of Huperzine A for 180 days and iv injections of 0.3 mg/kg and 0.6 mg/kg of Huperzine A for 90 days. The control group was given im injections of distilled water. Three of the rabbits given im injections of 0.6 mg/kg of Huperzine A died between 66-136 days of taking the drug, but no toxic reactions were observed before they died. Ten dogs were separately given im injections of 0.3 and 0.6 mg/kg (3 dogs each) of Huperzine A and distilled water (4 dogs) for the control group for 180 days. No abnormalities were observed in the group given small dosages, but at the 0.6 mg/kg dose there was noticeable whole body muscle fiber twitching. The symptoms gradually decreased and disappeared following the length of the time the drug was given. The ECG showed no drug induced abnormalities. When the time arrived, the rabbits and dogs were dissected. The routine blood tests glutamic-pyruvic transaminase, zinc turbidity, urea nitrogen and creatinine were all normal. Each organ section was observed microscopically and a small number of rabbits in the group given the drug had myocardial cell denaturization atrophy and interstitial growth focus in their hearts. The hearts of the dogs had light fat infiltration. The cerebral cortex of each dosage group of rabbits and dogs had cerebral spongiocyte growth and myophagia, but the nerve pronuclei did not show any retrogression. This shows that when a relatively large dosage of Huperzine A was used for a longer period of time, this could affect the nervous systems of the heart and brain. The stimulation of the latter was even more outstanding.

TABLE 4

Acute Toxicity of Huperzine A on Mice and Rats

| Drug | Animal | Means Drug Was Given | LD$_{50}$ (95% fiducial Limits, mg/kg) | Toxic Strength |
|---|---|---|---|---|
| Huperzine A | Mice | sc | 3.0 (2.2–4.1) | 1.00 |
| " | " | ig | 5.2 (3.8–7.2) | |
| " | " | iv | 0.63 (0.58–0.68) | |
| " | " | ip | 1.8 (1.6–2.2) | |
| Physostigmine | " | ip | 0.8 (0.7–1.0) | 2.25 |
| Galanthamine | " | ip | 13.4 (11.3–16.0) | 0.13 |
| Huperzine A | Rats | ig | 25.9 (23.2–29.0) | 1.00 |
| " | " | iv | 2.5 (2.3–2.7) | |
| " | " | ip | 5.0 (4.2–5.9) | |
| Physostigmine | " | ip | 2.4 (2.3–2.6) | 2.08 |
| Galanthamine | " | ip | 22.9 (20.3–25.9) | 1.22 |

3. Mutation Tests

The Ames method as well as the two types of bacteria TA$_{98}$ and TA$_{100}$ which carry different mutation R factors were used to evaluate mutagenicity when combined with a metabolic activation system (S$_9$ mixed liquid). Four dosages of Huperzine A, 1, 10, 100 and 1,000 μg/container, were used and compared with a cyclophosphamide and a mutation group. Each dosage was run in triplicate with TA$_{98}$ or TA$_{100}$ and an automatic colony counter was used to count the number of reverse mutation colonies. The test results showed that there were no noticeable differences between Huperzine A and the spontaneous reverse mutation colony number. Further, the colony number of the positive control drug (cyclophosphamide) was greater than that of the spontaneous reverse mutation group (Table 5).

TABLE 5

Mutation Tests of Huperzine A (X ± SD)

| Drug | Dosage (μg/container) | TA$_{98}$ ± S$_d$ | TA$_{100}$ ± S$_d$ |
|---|---|---|---|
| Mutation | — | 18 ± 13 | 150 ± 75 |
| Huperzine A | 1 | 24 ± 7* | 117 ± 22* |
| | 10 | 30 ± 17* | 85 ± 24* |
| | 100 | 33 ± 6* | 101 ± 25* |
| | 1000 | 23 ± 7* | 91 ± 25* |
| Cyclophosphamide | 1500 | | 566 ± 10** |

Compared with spontaneous reverse mutation. *p > 0.05. **p < 0.05.

4. Teratological Tests

6–15 days after mice became pregnant they were given ip injections of Huperzine A and 7–18 days after rabbits became pregnant they were given im injections of Huperzine A. The results showed that the number of embryo absorptions and stillborn fetuses for the mice given ip injection of 0.19–0.38 mg/kg of Huperzine A was markedly greater than those of the control group (P<0.01). The results of a single ip injection of 0.38 mg/kg of Huperzine A on the tenth day of pregnancy were similar to that obtained when the drug was given many times (Table 6). Neither of the two methods of giving the drug resulted in abnormal embryos seen with the positive drug control of cod-liver oil (each gram contained 50,000 international units of Vitamin A and 5,000 international units of Vitamin D). The latter produced various types of externally observed deformities: short tails (44/97), short and no tails (18/97), back legs reversed (13/97), open eyes (7/97), exposed brains and spina bifida (1/97), sunken noses (1/97) and cleft palates (39/40). The number of stillborn fetuses among the rabbits given im injections of 0.08 mg/kg of Huperzine A was noticeably higher (P<0.05) than that of the control group. The other dosage groups both higher and lower had values close to those of the control group (P<0.05) (Table 6). No external, internal organ or skeletal deformities were observed for any of the dosages.

TABLE 6

The Effects of Huperzine - A on the Fetus of Pregnant Mice and Rabbits.

| (1) | (2) | (3) (mg/kg) | (4) | (5) | (6) | | | | |
|---|---|---|---|---|---|---|---|---|---|
| | | | | | (7) | (8) (g) | (9) (cm) | (10) | (11) |
| | (14) | ip | 6–15 | 16 | 10 ± 2 | 1.04 ± 0.13 | 2.1 ± 0.2 | 0.13 ± 0.34 | 0.06 ± 0.25 |
| (12) | "A" | 0.019 ip | " | 9 | 8 ± 3 | 1.24 ± 0.22 | 2.2 ± 0.3 | 1.0 ± 1.7 | 0.22 ± 0.44 |
| | " | 0.038 ip | " | 12 | 8 ± 2 | 1.2 ± 0.2 | 2.2 ± 0.3 | 0.5 ± 0.8 | 0.22 ± 0.44 |
| | " | 0.08 ip | " | 9 | 9 ± 2 | 1.2 ± 0.1 | 2.3 ± 0.1 | 0 | 0.17 ± 0.39 |
| | " | 0.19 ip | " | 15 | 9 ± 4 | 1.0 ± 0.2 | 2.1 ± 0.2 | 0.73 ± 1.7*** | 0.13 ± 0.35 |
| | " | 0.38 ip | " | 10 | 6 ± 4 | 1.1 ± 0.3 | 2.0 ± 0.3 | 2.1 ± 2.4*** | 0.8 ± 1.1*** |
| | " | 0.39 ip | 10 | 8 | 8 ± 4 | 0.95 ± 0.18 | 1.9 ± 0.1 | 0.75 ± 1.0*** | 0.9 ± 1.1*** |
| | (15) AD | 0.3 ml/ig | 8–10 | 17 | 6 ± 5 | 1.2 ± 0.1 | 2.2 ± 0.1 | 3.3 ± 4.5 | 0 |
| | (16) | 0.5 ml im | 7–18 | 4 | 9.2 ± 0.5 | 43.9 ± 8.2 | 8.9 ± 0.9 | 0 | 0.25 ± 0.5 |
| (13) | "A" | 0.2 im | " | 3 | 9.3 ± 0.6 | 40.2 ± 2.4 | 8.9 ± 0.1 | 0 | 0.7 ± 0.6 |
| | " | 0.08 im | " | 6 | 6.7 ± 2.5 | 41.2 ± 3.9 | 9.1 ± 0.3 | 0 | 1.2 ± 1.2** |
| | " | 0.04 im | " | 3 | 7.3 ± 3.8 | 48.0 ± 3.2 | 9.0 ± 0.8 | 0 | 0.7 ± 1.2 |
| | " | 0.02 im | " | 2 | 7.0 ± 1.4 | 42.3 ± 10.4 | 8.8 ± 0.4 | 0 | 0 |

**p < 0.05.
***p < 0.01
A-Huperzine - A
Key: (1) Animal; (2) Drug; (3) Dosage; (4) First day drug given after pregnancy; (5) Number of pregnant animals; (6) Fetus of mice (rabbits); (7) Number of fetuses; (8) Body weight; (9) Body length; (10) Number absorbed; (11) number of stillbirths; (12) Mice; (13) Rabbits; (14) Distilled water; (15) Vitamin A and D titrant; (16) Distilled water.

OBSERVATIONS ON THE CLINICAL CURATIVE EFFECTS OF HUPERZINE A ON 128 CASES WITH MYASTHENIA GRAVIS

In order to further verify Huperzine A's clinical curative effects and observe its side effects, trials were undertaken to observe the similarities and differences between Huperzine A and neostigmine. 128 patients with correctly diagnosed myasthenia gravis were used in the trial. 69 of these patients took neostigmine as a control group and 59 patients used Huperzine A exclusively. The conditions of the clinical use of Huperzine A for these 128 cases are set out hereafter.

I. METHODOLOGY

Patients affected with myasthenia gravis (MG) with typical clinical symptoms which improved after using neostigmine were the subjects for testing and verification. Intramuscular injections of Huperzine A were given each day and the curative effects and side effects were observed after the injections. It was generally used for at least ten days and each dosage was 0.4-0.5 mg. Neostigmine and Huperzine A were used to carry out double blind cross-over control trials wherein 0.4 mg of Huperzine A was injected for five days and 0.5 mg of neostigmine was injected for five days with alternating use of the drugs in the control group. The injections were all given in the morning and on the morning prior to the injections anticholinesterase drugs were discontinued. Neither the patients nor the doctors knew which drug was being injected. Later, the symptoms, the duration of the improvements, if any, which were obtained by the drugs and the side effects were recorded. Based on these factors, the relative merits of the two drugs were established.

II. THE SYMPTOM APPRAISAL STANDARDS (+) (++) and (+++) was used as the standard for the seriousness of the symptoms, (+++) was the most serious.

1. Prolapse of eyelids: the tear width of the eye after use of the drug was measured. If there was an increase of 0.2 cm above that before use of the drug, then the effect was "+", if the increase was 0.4 cm then the effect was "++" and if the increase was 0.6 cm then the effect was "+++".

2. Impairment to eyeball activity: when the eyeball was basically fixed and immovable then it was "+++", those who had reoccuring major complaints and basically normal activities were "+" and those in an intermediate state were "++".

3. Difficulties in swallowing: when swallowing was still possible but there was a feeling of difficulty or there was slowing of the speed of the intake of food then the patient was treated as "+"; when the patient could swallow but it was very slow then the patient was "++"; when the patient was basically unable to swallow the rating was "+++".

4. Systemic myasthenia: patients who were able to walk but felt very exhausted were "+"; patients who were able to stand up and walk with difficulty a short distance in the ward or corridor were "++"; and patients who could not get out of bed were "+++".

III. CLINICAL DATA

1. Age, Sex, Type and the Course of the Disease

Based on the clinical symptoms, those patients who only had their extra-ocular muscles affected were of the eye muscle type, 83 cases (64.85%) in this group. Those who mainly had tired muscles when swallowing were of the medulla oblongate type, 10 cases (7.81%) in this group. Those who had tired muscles in the four limbs were of the systemic type, 35 cases (27.34%) in this group. The shortest course of the disease was 3 days, the longest 23 years and the average was about 33 months.

62 of the cases in this group were male and 66 were female. The youngest male patient was one year old and the oldest was 80. The youngest female patient was 3 years old and the oldest was 74. The average male and female age was 27.39 years of age.

2. Results After the Use of Huperzine A (1) Aside from one of the 128 cases, all of the other patients had reactions to the Huperzine A as regards the physical symptom initial improvement time and the optimal curative effect time. The shortest physical symptom initial improvement time was 10 minutes after injection. An individual case had the longest of 3.7 hours before there were effects. The average was 21.92±19.56 minutes. 108 of the cases (85.03%) had effects within 15-30 minutes.

As regards the occurence of the time maximal effect among 127 of the cases for which the drug was effective, the shortest was 18 minutes, the longest was 240 minutes and the average was 50.34±25.65 minutes. 65 cases (51.18%) had the optimal curative effect occur within 45-60 minutes after using the drug. See Table 7.

TABLE 7

The physical symptom improvement initial times and optimal curative effect times of 127 cases with MG.

| Type/Time | Shortest (Minutes) | Longest (Minutes) | Average (Minutes) X = SD | 15-30 Minutes No. of Cases | % | 45-60 Minutes No. of Cases | % |
|---|---|---|---|---|---|---|---|
| Initial effect time | 10 | 222 | 21.92 = 19.56 | 108 | 85.03 | | |
| Maximal effect time | 18 | 240 | 50.34 ± 25.65 | | | 65 | 51.18 |

2. The sustaining time of the effects of Huperzine A: the shortest sustaining time of the effect of Huperzine A was 0.66 hours and this was a patient on the eye muscle type. The longest was 24 hours and this was observed in the systemic type as well as the eye muscle type. The average action time was 5.94±4.92 hours. The action time of 44 cases (34.64%) reached 4-6 hours while the action time of 40 cases (31.64%) exceeded 6 hours. The shortest time among these 40 cases was 6 hours, and the longest was twenty-four (24) hours, average was 10.42±5.80 hours.

3. Effects

Aside from one case, the drug was effective for the other 127 cases (99.21%). Among these, 71 cases (55.46%) had marked effects and it was effective for 56 cases (43.75%).

4. Laboratory Examinations

Albumin, hemochrome, blood platelet, routine urine, liver function and EKG examinations on some of the 128 cases given Huperzine A before and after they took the drug were carried out and none of them showed any noticeable differences in albumin, blood patelets and routine urine tests before and after being injected. The white blood cells noticeably decreased after the injections and this occurred in only 2 cases (2.4%). 2 cases had abnormal liver functions before the injections and both of these cases had normal liver functions after the injections. However, there were also 2 cases (2.2%)

which had normal liver functions before the injections but the SGPT was abnormal after the injections.

The EKGs of 96 patients before the injections of Huperzine A were recorded and among these 11 cases (11.45%) were abnormal. The EKGs of 72 patients after the injections of Huperzine A were recorded and among these 11 cases (15.27%) were abnormal. 9 of these 11 were among the original abnormal group and only 2 cases (2.7%) were normal before the injections (see Table 8).

TABLE 8

EKG changes before and after the injections.

| Sex | Age | EKG Manifestations Before the Injections | Manifestations After the Injections |
|---|---|---|---|
| Female | 24 | Right bundle-branch Block | Same |
| Female | 50 | Incomplete left bundle branch block | Same |
| Male | 22 | Pre-excitation Syndrome | Same |
| Male | 31 | High voltage | Same |
| Male | 56 | Ventricular flutter | Abnormal |
| Male | 34 | Frequent early ventricular plus | Same |
| Female | 74 | Atrial trembling | Same |
| Male | 80 | Frequent early ventricular pluse | Same |
| Male | 60 | The left ventricle had high voltage | Same |
| Male | 16 | Slight abnormality | Normal |
| Female | 33 | Slight abnormality | No follow up visit |
| Female | 24 | Normal | ST section change |
| Female | 33 | Normal | Light T wave change |

5. Comparison of the Effects of Huperzine A and Neostigmine (1) Comparison of the maintained times of the effects. Control tests were carried out on 69 cases. The action time Huperzine A was longer than that of neostigmine for 58 cases (84.05%) of the action time of neostigmine was longer than that of Huperzine A in 6 cases (8.69%). The action times of the two drugs were close in 5 cases (7.26%). After statistical analyses, there were very significant differences between the two ($X^2 = 78.52$, $p < 0.0001$).

Among the 58 cases wherein the action time of the Huperzine A was longer than that of neostigmine, the shortest difference was 0.05 hours, the longest was 20 hours and the average was 2.90±3.64 hours (see Table 9).

TABLE 9

Specific conditions of 58 cases when the action time of Huperzine-A was longer than that of neostigmine

| Time | Difference within 2 Hours | Difference 2–4 Hours | Difference 4–6 Hours | Difference over 6 hours | Average Difference X ± SD (hours) |
|---|---|---|---|---|---|
| 58 cases | 29 | 18 | 4 | 7 | 2.90 + 3.64 |
| % | 50 | 31.03 | 6.89 | 12.08 | |

Among the 6 cases wherein the action time of the Huperzine A was less than that of the neostigmine, the shortest was 0.3 hours and the longest was 6 hours. Four of these cases were within one hour while the other two were 1.6 and 6 hours.

(2) Comparison of the action strengths: the injected dosage of Huperzine A was 0.4 mg whereas 0.5 mg of neostigmine was used. Given these dosages, the action of the former was stronger than that of the latter in 16 of the cases. The action strength of the former was lower than that of the latter in 7 cases. There were basically no differences between the two in 46 of the cases and it can therefore be said that under these dosages the action strengths of both are not very different.

(3) Comparison of the side effects: among control patients, 34 cases had side effects from the neostigmine (49.27%) whereas 45 cases (65.21%) had side effects from the injections of Huperzine A. Statistical analyses showed that there were no significant differences ($X^2 = 3.58$, $P > 0.05$).

Among the more frequently occuring side effects were perspiring, nausea and blurred vision. These three revealed marked differences statistically between the two drugs (these were separately nausea $X^2 = 15$, $P < 0.001$; perspiring $X^2 = 5.5$, $P < 0.01$; blurred vision $X^2 = 12.96$, $P < 0.001$). There were no marked differences in the occurrence rates of other side effects. Therefore, neostigmine more noticeably than Huperzine A caused perspiring and blurred vision but Huperzine A was more apt to cause nausea than was neostigmine. If one compares the use of Huperzine A for 128 patients and the use of neostigmine for 69 cases, only in the area of nausea was the percentage of its occurrence greater than that of neostigmine. There was significant statistical difference ($X^2 = 4.99$, $P < 0.05$). The Huperzine A had lower side effects for each of the other items than neostigmine including muscle bundle quivering, dizziness, perspiring and blurred vision. Statistical analysis showed significant difference. ($x^2 = 4.18$, $P < 0.05$, $x^2 = 36.25$, $P < 0.001$, $X^2 = 25.23$, $P < 0.001$, $X^2 = 46.52$, $P < 0.0001$ respectively.) See Table 10. Both the statistics and processing showed noticeable differences and we can thus basically come to the conclusion the Huperzine A is superior to neostig-mine. This is especially true as regards the action time length of Huperzine A which is its outstanding feature. This is actually the major drawback in the clinical use of neostigmine.

(4) Comparison between Huperzine A and neostigmine: Based on the above facts, the effective time of Huperzine A was significantly larger than neostigmine. The frequency of the various side effects, especially muscle bundle quivering, dizziness, perspiration, and blurred vision; Huperzine A was statistically lower than neostigmine.

Based on the above data on this group of 128 patients, it can be considered that Huperzine A is an effective anticholinesterase drug for treating myasthenia gravis. It did not have any significant negative effects on the major organs, for example, lungs, kidney, heart and the hematopoietic systems, and the clinical occurrence rate of side effects was low. Aside from nausea, it had lower side effects in all other areas than neostigmine. Moreover, the fact that its curative effect action time was noticeably longer than that of neostigmine is its major outstanding feature.

TABLE 10

Comparison of the side effects between neostigmine and Huperzine A

| (33) | (3) | (2) | (7) (20)% | | (8) (21)% | | (9) (22)% | | (10) (23)% | | (11) (24)% | | (12) (25)% | | (13) (26)% | | (14) (27)% | | (15) (28)% | | (16) (29)% | | (17) (30)% | | (18) (31)% | | (19) (32)% | |
|---|---|---|---|---|---|---|---|---|---|---|---|---|---|---|---|---|---|---|---|---|---|---|---|---|---|---|---|
| (34) | 59 | 356 (4) | 37 | 10.4 | 72 | 20.3 | 13 | 3.7 | 25 | 7.0 | 46 | 12.9 | 21 | 5.9 | 10 | 2.8 | 9 | 3.5 | 3 | 0.8 | 13 | 3.0 | 11 | 3.1 | 10 | 2.8 | 11 | 3.2 |
|  | 69 | 349 (5) | 29 | 8.3 | 68 | 19.5 | 14 | 4.0 | 43 | 12.1 | 15 | 4.3 | 26 | 7.4 | 6 | 1.2 | 11 | 1.2 |  |  | 12 | 3.4 |  |  | 7 | 2.0 | 24 | 9.7 |
| (35) | 128 | 1226 (6) | 4.0 | 3.3 | 100 | 8.1 | 38 | 3.1 | 59 | 4.8 | 95 | 7.8 | 80 | 6.5 | 15 | 1.2 | 25 | 2.0 | 5 | 0.4 | 13 | 1.0 | 13 | 1.0 | 11 | 0.5 | 22 | 1.8 |

Key: (1) Type of side effect; (2) number of occurrences; (3) Number of cases (number of injections); (4) 69 cases used Huperzine A 355 times; (5) 69 cases used neostigmine 349 times; (6) 128 cases used Huperzine A 1,225 times; (7) Muscle bundle quivering; (8) Dizziness; (9) Tinnitus; (10) Perspiring; (11) Nausea; (12) Abdominal pains; (13) Vomiting; (14) Drooling; (15) Disturbed sleep; (16) Myosis; (17) Changes in the rhythm of the heart; (18) Increase in the number of bowel movements; (19) Blurred vision; (20)-(32) Number of times; (33) Group; (34) Control group; (35) Non-control group.

Based on the fact that Huperzine A possesses definite pharmacodynamic activity and a relatively large therapeutic index, it was clinically tested. The results of the treatment of 128 cases with myasthenia gravis showed that the intramuscular injections of 0.4 mg. of Huperzine A were able to definitely improve the myasthenia gravis condition of the patients, its sustained time of action was longer than that of neostigmine and it had lower side effects. The intramuscular injections of 25 or 50 μg of Huperzine A in 58 cases of cerebral arteriosclerosis accompanied by senile dementia was effective in improving memory functions.

A compound of formula I, II or III, or a salt thereof, or a composition containing a therapeutically effective amount of a compound of formula I, II or III, or a salt thereof can be administered by methods well known in the art. Thus, a compound of formula I, II or III, or a salt thereof can be administered either singly or with other pharmaceutical agents, for example, orally, parenterally or rectally. For oral administration they can be administered in the form of tablets, capsules, for example, in admixture with talc, starch, milk sugar or other inert ingredients, that is, pharmaceutically acceptable carriers, or in the form of aqueous solutions, suspensions, elixirs or aqueous alcoholic solutions, for example, in admixture with sugar or other sweetening agents, flavoring agents, colorants, thickeners and other conventional pharmaceutical excipients. For parenteral administration, they can be administered in solution or suspension, for example, an aqueous or peanut oil solution or suspension using excipients and carriers conventional for this mode of administration.

In the practice of the invention, the dose of a compound of formula I, II or III, or a salt thereof to be administered and the frequency of administration will be dependent on the potency and duration of activity of the particular compound of formula I, II or III, or salt to be administered and on the route of administration, as well as the severity of the condition, age of the mammal to be treated and the like. Doses of a compound of formula I or a salt thereof contemplated for use in practicing the invention for the treatment of myasthenia gravis are in the range of from about 0.01 to about 25 mg per day, preferably about 0.1 to about 10 mg either as a single dose or in divided doses, and for the treatment of senile dementia are in the range of from about 0.10 to about 100 mg. per day, preferably about 1.0 to about 50 mg. either as a single dose or in divided doses.

The Examples which follow further illustrate the invention. All temperatures are in degrees centigrade, unless otherwise stated.

EXAMPLE 1

Isolation of (5R, 9R, 11E)-5-amino-11-ethylidene-5,6,10-tetrahydro-7-methyl-5,9-methanocycloocta[b]pyridin-2(1H)-one (Huperzine A)

About 100 kg dry weight of the crushed, powdered plant: Huperzia serrata (Thunb.) Trev., was placed in a container, and extracted with refluxing 95% ethanol several times. The combined ethanol extracts were evaporated to a residue which was suspended in dilute aqueous hydrochloric acid (1-2%) and extracted with ethyl ether to remove impurities. The aqueous layer was then neutralized with concentrated aqueous ammonia and the total alkaloids were extracted into chloroform. After partially concentrating the chloroform solution, the solution was repeatedly extracted with 1% sodium hydroxide. The sodium hydroxide layer was then neutralized with concentrated hydrochloric acid, and again brought back to pH greater than 10 with concentrated ammonia. This aqueous solution was extracted with chloroform and the residue from the chloroform extracts was chromatographed on silica gel column. Solvent system used was chloroform-methanol, 98:2; 97:3; and 96:4 ratio in succession. Fractions from the chromatography were analyzed by TLC and those with a single spot were combined. After solvent removal, the residue was crystallized from acetone to give crude (5R, 9R, 11E)-5-amino-11-ethylidene-5,6,9,10-tetrahydro-7-methyl-5,9-methanocycloocta[b]pyridin-2(1H)-one (Huperzine A), about 10 g; yields ran 0.008% to 0.011% of starting dry powdered plant.

The crude Huperzine A was analyzed to be about 95% pure or better and contained about 2% (4aR, 5R, 10bR)-1,2,3,4,4a,5,6,10b-octahydro-12-methyl-5,10b-propeno-1,7-phenanthrolin-8(7H)-one (Huperzine B). This material with a mp of 221°-229° C., was used in clinical trials.

To further purify Huperzine A, the crude material was rechromatographed using the chloroform: methanol solvent mixture or recrystallized from methanol/acetone mixture. The pure material has mp 230° C.

m. wt. $C_{15}H_{18}N_2O$; 242.1426 (By mass spectroscopy).

$[\alpha]_D^{25} - 150.4°$ (conc. 0.498 in methanol).

UV max. (ethanol) 231 nm (log ε 4.01); 313 nm (log ε 3.89).

IR: 1650, 1550, 3480, 3340, 3269 $cm^{-1}$.

EXAMPLE 2

Isolation of (4aR, 5R, 10bR)-1,2,3,4,4a,5,6,10b-octahydro-12-methyl-5,10b-propeno-1,7-phenanthrolin-8(7H)-one (Huperzine B)

The crude material isolated from later fractions of the chromatograph column was found to be a minor component. Further purification involved rechromatographing on silica gel using a solvent system of chloroform-acetone-methanol in 50:47:3 ratio. The material collected from the column was recrystallized from acetone to give pure (4aR, 5R, 10bR)-1,2,3,4,4a,5,6,10b-octahydro-12-methyl-5,10b-propeno-1,7-phenanthrolin-8(7H)-one (Huperzine B). m.p. 270°–271° C.

m. wt. $C_{16}H_{20}N_2O$; 256.1558 (by mass spectroscopy).
$[\alpha]_D^{25}$ −54.2° (conc. 0.203% in methanol).
Yield 0.000833% based on dry plant ($8.33 \times 10^{-6}$).

EXAMPLE 3

Preparation of (5R, 9R, 11E)-11-ethylidene-5,6,9,10-tetrahydro-7-methyl-5-(methylamino)-5,9-methanocycloocta[b]pyridin-2(1H)-one The mono-methyl derivative of Huperzine A was prepared from Huperzine A (150 mg.) by the treatment with methyl iodide (1 ml.) in methanol (0.5 ml.) and acetone (2 ml.) overnight. After concentrating, product was recrystallized from acetone (yield 120 mg.)
mp 235°–236° C.
MS 256 (M−).

EXAMPLE 4

Preparation of (5R, 9R, 11E)-11-ethylidene-5,6,9,10-tetrahydro-7-methyl-5-(dimethylamino)-5,9-methanocycloocta[b]pyridin-2(1H)-one The di-methyl derivative of Huperzine A was obtained by the treatment of Huperzine A (150 mg.) with formic acid (88%, 1 ml.) and formaldehyde (35%, 1 ml.) at 100° C. for 4 hours. After concentrating under reduced pressure and basifying with conc. ammonium hydroxide, the desired product was extracted with chloroform. Recrystallization from a chloroform-methanol mixture gave pure title compound (yield 150 mg.).
mp 243°–245° C.
MS 270 (M+).

EXAMPLE 5

Preparation of (5R, 9R, 11E)-11-ethylidene-5,6,9,10-tetrahydro-1,7-dimethyl-5-(dimethylamino)-5,9-methanocycloocta[b]pyridin-2(1H)-one The title trimethyl derivative of Huperzine A was obtained by methylation of Huperzine A (150 mg.) with dimethyl sulfate (3 ml.) in acetone (10 ml.) and 20% aqueous sodium hydroxide (4 ml.) at reflux. After three (3) hours, the mixture was extracted with chloroform. TLC analysis of this extract showed two spots. Purification by silica gel column chromatography (chloroform as solvent, impurity being eluted first) gave the trimethyl derivative as an oil (yield 110 mg.). The title compound is an oil.
MS 284 (M+).

EXAMPLE 6

Preparation of (4aR, 5R, 10bR)-1,2,3,4,4a,5,6,10b-octahydro-1,12-dimethyl-5,10b-propeno-1,7-phenanthrolin-8(7H)-one Methylation of Huperzine B (150 mg) according to the method as utilized in Example 4 gave (4aR, 5R, 10bR)-1,2,3,4,4a,5,6,10b-octahydro-1,12-dimethyl-5,10b-propeno-1,7-phenanthrolin-8(7H)-one, recrystallized from methanol (yield 150 mg.).
m.p. 272°–273° C.
MS 270 (M+).

EXAMPLE 7

Preparation of (4aR, 5R, 10bR, 12S)-1,2,3,4,4a,5,6,10b-octahydro-1,12-dimethyl-10b,5-propano-1,7-phenanthrolin-8(7H)-one Monomethyl Huperzine B (140 mg.) was hydrogenated in the presence of platinum oxide (100 mg.) and acetic acid (5 ml.). After basification with ammonium hydroxide and extraction into chloroform, the title product was recrystallized from chloroform-methanol (yield 130 mg.).
m.p. 281°–3° C.
MS 272 (M−).

EXAMPLE 8

Preparation of (5R, 9R)-5-amino-11-ethyl-5,6,9,10-tetrahydro-7-methyl-5,9-methanocycloocta[b]pyridin-2(1H)-one Hydrogenation of Huperzine A (150 mg.) in the presence of platinum oxide (60 mg.) in ethanol (20 ml.) gave the title dihydrohuperzine A, where the former exo-double bond is saturated. This material was purified by silica gel column chromatography (chloroform-methanol, 15:1 as solvent) followed by recrystallization from methanol-acetone (yield 100 mg).
m.p. 269°–270° C.
MS 244 (M−).

EXAMPLE 9

Preparation of (5R, 9R)-5-amino-11-ethyl-5,6,7,8,9,10-hexahydro-7-methyl-5,9-methanocycloocta[b]pyridin-2(1H)-one Huperzine A (200 mg.) was hydrogenated in the presence of platinum oxide (100 mg.) and acetic acid (10 ml.). After basification and extraction into chloroform, the title tetrahydrohuperzine A was recrystallized from a methanol-acetone mixture (yield 180 mg.).
m.p. 264°–5° C.
MS 246 (M+).

EXAMPLE 10

Preparation of (5R, 9R, 11E)-5-(acetylamino)-11-ethylidene-5,6,9,10-tetrahydro-7-methyl-5,9-methanocycloocta[b]pyridin-2(1H)-one The titled N-acetyl Huperzine A derivative was prepared by treating Huperzine A (100 mg.) with acetic anhydride (1 ml.) and pyridine (0.5 ml.) at room temperature for one week. This mixture was poured into ice-water and extracted with chloroform. The chloroform extract was concentrated and purified by silica gel column chromatography (chloroform-methanol, 15:1 as solvent) and recrystallization from acetone (yield 100 mg.).

m.p. 276°-7° C.
MS 284 (M−).

EXAMPLE 11

An injection of the following composition is prepared in the usual manner:

| | |
|---|---|
| (5R,9R,11E)-5-amino-11-ethylidene-5,6,9,10-tetrahydro-7-methyl-5,9-methanocycloocta[b]2(1H)-one hydrochloride | 50 mg. |
| Water for injection q.s. ad | 2.00 ml. |

We claim:

1. Essentially pure (4aR, 5R, 10bR)-1,2,3,4,4a,5,6,10b-octahydro-12-methyl-5,10b-propeno-1,7-phenanthrolin-8(7H)-one.

2. A pharmaceutically acceptable acid addition salt of (4aR, 5R, 10bR)-1,2,3,4,4a,5,6,10b-octahydro-12-methyl-5,10b-propeno-1,7-phenanthrolin-8(7H)-one.

3. A compound of the formula

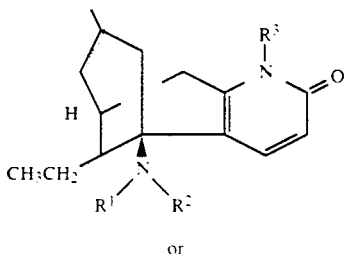

II or

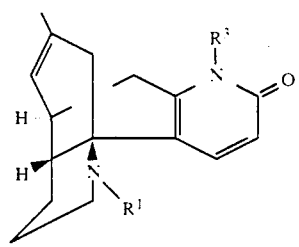

III wherein R¹, R² and R³ independently are hydrogen or lower alkyl, the dotted ( ... ) line is an optional double bond, and provided that in formula III one of R¹, R² and R³ is other than hydrogen, or a pharmaceutically acceptable acid addition salt thereof.

4. A compound, in accordance with claim 3, of the formula

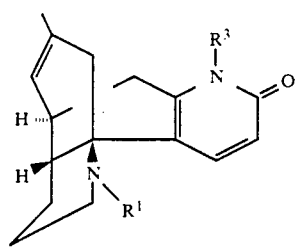

III wherein R¹ and R² independently are hydrogen or lower alkyl, and provided that one of R¹ and R² is other than hydrogen, or a pharmaceutically acceptable acid addition salt thereof.

5. A compound, in accordance with claim 4, (4aR, 5R, 10bR)-1,2,3,4,4a,5,6,10b-octahydro-1,12-dimethyl-5,10b-propeno-1,7-phenanthrolin-8(7H)-one.

6. A compound, in accordance with claim 3, of the formula

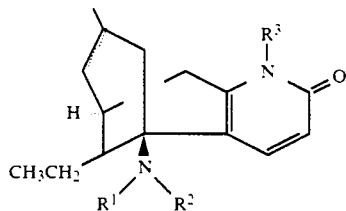

II wherein R¹, R², and R³ independently are hydrogen or lower alkyl, and the dotted ( ... ) line is an optional double bond, or a pharmaceutically acceptable acid addition salt thereof.

7. A compound, in accordance with claim 6, (5R, 9R)-5-amino-11-ethyl-5,6,9,10-tetrahydro-7-methyl-5,9-methanocycloocta[b]pyridin-2(1H)-one.

8. A compound, in accordance with claim 6, (5R, 9R)-5-amino-11-ethyl-5,6,7,8,9,10-hexahydro-7-methyl-5,9-methanocycloocta[b]pyridin-2(1H)-one.

9. A pharmaceutical composition comprising an effective amount of an essentially pure compound of a formula

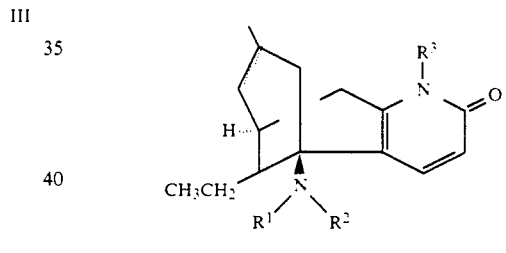

II or

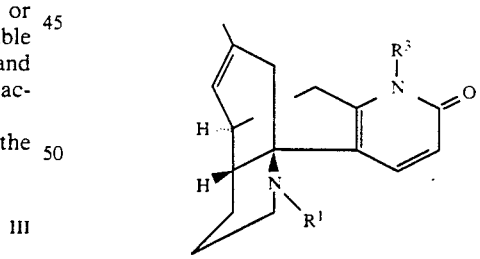

III wherein R¹, R² and R³ independently are hydrogen or lower alkyl, and the dotted ( ... ) line is an optional double bond, or a pharmaceutically acceptable acid addition salt thereof and an inert pharmaceutical carrier.

10. A pharmaceutical composition, in accordance with claim 9, wherein the compound is (4aR, 5R, 10bR)-1,2,3,4,4a,5,6,10b-octahydro-12-methyl-5,10b-propeno-1,7-phenanthrolin-8(7H)-one.

* * * * *